United States Patent [19]

Ferreira et al.

[11] 4,396,769
[45] Aug. 2, 1983

[54] PROCESS FOR PREPARING CRYSTALLINE, NON-DUSTING BIS(2,2,6,6-TETRAMETHYLPIPERIDIN-4-YL) SEBACATE

[75] Inventors: Anibal L. Ferreira, Warwick; Robert E. Stahlbush, Cranston, both of R.I.

[73] Assignee: Ciba-Geigy Corporation, Ardsley, N.Y.

[21] Appl. No.: 347,751

[22] Filed: Feb. 11, 1982

[51] Int. Cl.$^3$ ............................................ C07D 211/46
[52] U.S. Cl. ..................................................... 546/188
[58] Field of Search ............................................ 546/188

[56] References Cited

U.S. PATENT DOCUMENTS 3,640,928  2/1972  Murayama et al. ............... 546/188

OTHER PUBLICATIONS

Weissburger, "Technique of Organic Chemistry", vol. III, pp. 445–451 (1950), (Interscience).

*Primary Examiner*—Robert T. Bond
*Attorney, Agent, or Firm*—Luther A. R. Hall

[57] ABSTRACT

Crystalline, non-dusting bis(2,2,6,6-tetramethylpiperidin-4-yl) sebacate is made by heating the sebacate ester to a temperature above its melting point and then slowly cooling the melt with agitation to form the product in a crystalline, non-dusting form. This ester, also known as TINUVIN 770, is a valuable commercial light stabilizer for a myriad of substrates.

4 Claims, No Drawings

PROCESS FOR PREPARING CRYSTALLINE, NON-DUSTING BIS(2,2,6,6-TETRAMETHYLPIPERIDIN-4-YL) SEBACATE

FIELD OF THE INVENTION

This invention pertains to a method of preparing bis(2,2,6,6-tetramethylpiperidin-4-yl) sebacate, the commercial light stabilizer TINUVIN 770, is a crystalline, non-dusting form having a particle size greater than 100 microns.

BACKGROUND OF THE INVENTION

Among the light stabilizers enjoying great commercial success is bis(2,2,6,6-tetramethylpiperidin-4-yl) sebacate, TINUVIN 770, available from CIBA-GEIGY Corporation. The preparation of this sebacate ester is described in U.S. Pat. No. 3,640,928 by the reaction of 2,2,6,6-tetramethylpiperidin-4-ol with an appropriate sebacic acid derivative.

Isolation and purification of the desired sebacate ester by conventional crystallization methods leads to a product obtained as friable thin flakes with severe dusting problems. While this dusting propensity in no way affects adversely the light stabilization efficacy of this sebacate ester, it does lead to severe handling problems, potential health hazards and related economic barriers to the full realization of the economic potential of this effective light stabilizer in practical use.

OBJECTS OF THE INVENTION

The object of the invention is to provide a method of preparing bis(2,2,6,6-tetramethylpiperidin-4-yl) sebacate in a crystalline, non-dusting form.

A further object of the instant invention is a process to convert the crude sebacate ester product obtained from the reaction of 2,2,6,6-tetramethylpiperidin-4-ol and a sebacic acid derivative as a wet paste, containing about 5 to 10% by weight of organic hydrocarbon solvent and additionally containing small amounts of water directly into a crystalline, non-dusting product by a combined drying and melting step under vacuum conditions followed by a slow melt crystallization step.

DETAILED DISCLOSURE

The instant invention pertains to a process of preparing bis(2,2,6,6-tetramethylpiperidin-4-yl) sebacate in a crystalline, non-dusting form having a particle size greater than 100 microns and with a volatiles content less than 0.5% by weight, which comprises heating bis(2,2,6,6-tetramethyl-piperidin-4-yl) sebacate, in the form of a friable, dusting powder or wet paste, to above its melting point, at a temperature between 83° and 95° C., preferably between 83° and 88° C., under a pressure of 5 to 150 mm Hg, preferably of 5 to 50 mm Hg, with agitation to form a uniform melt of the sebacate, and then slowly cooling the melt, with continued agitation, to a temperature between 70° and 83° C., preferably between 72° and 74° C., to cause the sebacate to crystallize from the melt in a crystalline, non-dusting form. The crystalline mass is then cooled slowly in a programmed temperature gradient to room temperature using minimum agitation.

The instant process may be applied to any form of bis(2,2,6,6-tetramethylpiperidin-4-yl) sebacate, either pure and dry or crude and wet.

Pure, dry bis(2,2,6,6-tetramethylpiperidin-4-yl) sebacate isolated in a conventional manner, such as by recrystallization from n-heptane as friable thin flakes, i.e. in a dusting form, can serve as the starting material in the instant process. Since this product contains only adventitious amounts of any volatile material, there is no need for a strong vacuum (greatly reduced pressure) during the process as would be needed in the case where a large amount of volatiles were present as is discussed infra. However, the imposition of a vacuum presents no problem during the process and may be used beneficially even in the case of a dry sebacate ester starting material. The instant process affords a facile way of converting a friable thin flake, dusting product into a crystalline, non-dusting form, which exhibits crystal growth in all three dimensions with a markedly improved settling property.

Another particularly advantageous embodiment of the instant process is the aspect of applying the process directly to the crude sebacate ester product obtained from the reaction of 2,2,6,6-tetramethylpiperidin-4-ol and a sebacic acid derivative as a wet paste containing from 5 to 10% by weight of heptane or other hydrocarbon solvent and additionally containing small amounts of water to form the crystalline, non-dusting product with the concomitant removal of the solvent and water present.

With the considerable quantity of organic hydrocarbon solvent, preferably n-heptane, and some water present when the wet paste is used as the starting material in the instant process, it is expedient to use a reduced pressure (vacuum) throughout the instant process to facilitate the removal of the organic hydrocarbon solvent, water and any other volatiles from the sebacate ester. Indeed, the use of a pressure in the range of 5 to 150 mm Hg, preferably 5 to 50 mm Hg, proves most beneficial.

Any type of equipment which can provide concomitantly stirring or agitation, reduced pressure capability and good temperature control can be used for carrying out the instant process.

A preferred piece of equipment is a standard rotary dryer which provides all the essential operating capabilities needed in the instant process.

The following examples are presented for the purpose of illustration only and are not to be construed to limit the nature or scope of the instant invention in any manner whatsoever.

EXAMPLE 1

1360 Kg of a wet paste consisting of 95% by weight of bis(2,2,6,6-tetramethylpiperidin-4-yl) sebacate and 5% by weight of n-heptane and an adventitious amount of water was charged to a standard rotary dryer. Full speed agitation of the dryer was then begun and a reduced pressure (vacuum) of 5–50 mm Hg was then imposed. The temperature of the dryer was then raised to 75°–78° C. The contents of the dryer were kept under these operating conditions for a period of 2 hours to facilitate removal of the n-heptane and adventitious water present under vacuum conditions.

The temperature of the dried charge was then raised to 83°–86° C., just above the melting point of bis(2,2,6,6-tetramethylpiperidin-4-yl) sebacate, and the melted charge was stirred under vacuum for 2 hours at said temperature for complete liquefaction.

The melted charge was then allowed to cool to room temperature in stages over a 12-hour period with agitation likewise decreasing in stages over the same period. The charge was held at 75°–78° C. for 2 hours with moderate agitation, then to 70°–72° C. in 1–5 hours with slow agitation, then to 60° C. in 1–5 hours, preferably 5 hours, with slow agitation and finally to 25°–30° C. in 1–3 hours with very slow agitation.

The desired product was obtained in essentially quantitative yield based on the originally charged bis(2,2,6,6-tetramethylpiperidin-4-yl) sebacate as a crystalline, non-dusting product having particle size greater than 100 microns. The product is in the form of a thick non-dusting triclinic crystal resulting from crystal growth in all dimensions. These crystals are dimensionally stable as opposed to dusty, thin, flat, friable crystal flakes obtained by conventional crystallization.

EXAMPLE 2

When an equal weight of dry bis(2,2,6,6-tetramethylpiperidin-4-yl) sebacate in friable, dusting form was substituted for the wet paste used in Example 1, said friable, dusting sebacate ester was converted into a crystalline, non-dusting product using the general procedure of Example 1.

What is claimed is:

1. A process for preparing bis(2,2,6,6-tetramethylpiperidin-4-yl) sebacate in a crystalline, non-dusting form having a particle size greater than 100 microns and with a volatiles content less than 0.5% by weight, which comprises
   heating bis(2,2,6,6-tetramethylpiperidin-4-yl) sebacate, in the form of a friable, dusting powder or wet paste, to above its melting point, at a temperature between 83° and 95° C. under a pressure of 5 to 150 mm Hg with agitation to form a uniform melt of the sebacate, and then
   slowly cooling the melt, with continued agitation, to a temperature between 70° and 83° C. to cause the sebacate to crystallize from the melt in a crystalline, non-dusting form.
2. A process according to claim 1 wherein the bis(2,2,6,6-tetramethylpiperidin-4-yl) sebacate being heated is in the form of a wet paste.
3. A process according to claim 1 wherein the bis(2,2,6,6-tetramethylpiperidin-4-yl) sebacate being heated is in the form of a friable, dusting powder.
4. A process according to claim 1 wherein the sebacate in form of a powder or wet paste is heated at a temperature between 83° and 88° C. under a pressure of 5 to 50 mm Hg and is then slowly cooled with agitation to a temperature between 72° and 74° C. to effect crystallization into a crystalline, non-dusting form.

* * * * *